United States Patent [19]

Wheeler

[11] 4,035,361
[45] July 12, 1977

[54] BIS-TRIMETHYLSILYL CEFAMANDOLE AND PROCESS THEREFOR

[75] Inventor: William J. Wheeler, Indianapolis, Ind.

[73] Assignee: Eli Lilly and Company, Indianapolis, Ind.

[21] Appl. No.: 667,753

[22] Filed: Mar. 17, 1976

[51] Int. Cl.² .................................... C07D 501/04
[52] U.S. Cl. .......................... 260/243 C; 424/246
[58] Field of Search ............................... 260/243 C

[56] References Cited

U.S. PATENT DOCUMENTS 3,641,021  2/1972  Ryan .............................. 260/243 C
3,694,437  9/1972  Jackson ......................... 260/243 C Primary Examiner—Nicholas S. Rizzo
Attorney, Agent, or Firm—William B. Scanlon; Everet F. Smith

[57] ABSTRACT

Bis-trimethylsilyl cefamandole is useful for regenerating cefamandole of excellent purity.

3 Claims, No Drawings

BIS-TRIMETHYLSILYL CEFAMANDOLE AND PROCESS THEREFOR

BACKGROUND OF THE INVENTION

Cefamandole is a cephalosporin antibiotic which is useful for combating infectious diseases such as enterobacter infections as disclosed in U.S. Pat. No. 3,903,278. Cefamandole is 7-(D-mandelamido)-3-(1-methyl-1,2,3,4-tetrazol-5-yl)thiomethyl-3-cephem-4-carboxylic acid and was first disclosed by Ryan in U.S. Pat. No. 3,641,021, Example 5. The process for making cefamandole by acylating "tetrazole nucleus," 7-amino-3-(1-methyl-1,2,3,4-tetrazol-5-yl) thiomethyl-3-cephem-4-carboxylic acid, with D-anhydro O-carboxymandelic acid is described by Greene in U.S. Pat. No. 3,840,531. The silylation of a cephalosporin nucleus is described by Jackson in U.S. Pat. No. 3,671,449. Jackson also describes the acylation of a silylated cephalosporin nucleus in U.S. Pat. No. 3,694,437. German Offenlegungsschriff 2522997 (Derwent 81950W/50) discloses 7-(D-α-hydroxyphenylacetamido)-3-(6-hydroxypyridazin-3-yl or tetrazolo[4,5-b]-pyridazin-6-yl)thiomethyl-3-cephem-4-carboxylic acid compounds which are protected on the α-hydroxyl and carboxylic acid functions. The silylated compounds are merely mentioned as incidental intermediates to the final products. Their preparation or properties are not expressly described in the disclosure.

Cefamandole or its sodium salt in crude form are extremely difficult to purify by recrystallization. Therefore, a practical method of purification is necessary to provide the purity required for pharmaceutical preparations. Crystalline sodium cefamandole can be obtained from cefamandole acid provided the acid is in a pure state.

The use of silyl groups as protecting groups which can be easily removed is widely recognized in the art. However, silylated cephalosporin compounds are generally so unstable that relatively few of them have been characterized as such.

It is a purpose of this invention to provide a stable crystalline cefamandole silyl derivative which is readily converted to cefamandole acid of excellent purity. By the process of this invention crude lots of cefamandole can be converted to the silyl derivative or the silyl derivative can be prepared ab initio by silylation of the cephalosporin tetrazole nucleus followed by acylation with anhydro O-carboxymandelic acid.

The reagents used in the processes of this invention are either commercially available or described in the literature. Both N-trimethylsilylacetamide (MSA) and N,O-bis(trimethylsilyl)acetamide (BSA) are commercially available. The preparation of the acylating agent D-anhydro-O-carboxymandelic acid,

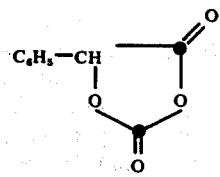

is described by Greene in U.S. Pat. No. 3,840,531, Example V.

SUMMARY OF THE INVENTION

This invention is concerned with the process for the preparation of bis-trimethylsilyl cefamandole represented by Formula I

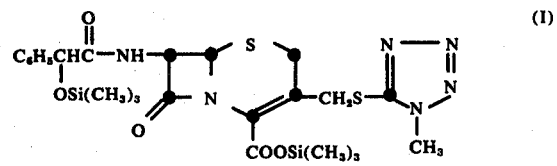

which comprises reacting 7-amino-3-(1-methyl-1,2,3,4-tetrazol-5-yl)thiomethyl-3-cephem-4-carboxylic acid with a silylating agent selected from N-trimethylsilylacetamide, N,O-bis(trimethylsilyl)acetamide, N,O-bis(trimethylsilyl)trifluoroacetamide, N-trimethylsilyl-N-methyltrifluoroacetamide or N-trimethylsilylimidazole and acylating the product so formed with D-anhydro O-carboxymandelic acid in substantially anhydrous ethyl acetate.

It is a further object of this invention to provide a process for the purification of crude cefamandole which comprises the steps of A. reacting 7-(D-mandelamido)-3-(1-methyl-1,2,3,4-tetrazol-5-yl)-3-cephem-4-carboxylic acid with a silylating agent selected from N-trimethylsilylacetamide, N,O-bis-(trimethylsilyl)acetamide, N,O-bis(-trimethylsilyl)trifluoroacetamide, N-trimethylsilyl-N-methyltrifluoroacetamide or N-trimethylsilylimidazole in substantially anhydrous ethyl acetate to provide trimethylsilyl 7-[D-(O-trimethylsilyl)mandelamido]-3-(1-methyl-1,2,3,4tetrazol-5-yl)thiomethyl-3-cephem-4-carboxylate; and B. reacting said silylated compound with a) water admixed with ethanol or isopropanol or b) isopropanol admixed with a primary alcohol selected from methanol, ethanol, propanol or butanol to provide 7-(D-mandelamido)-3-(1-methyl-1,2,3,4-tetrazol-5-yl)thiomethyl-3-cephem-4-carboxylic acid isopropyl solvate and reacting said isopropyl solvate with water; and recovering said cefamandole as a hydrate. The primary hydrolysis product of bis-trimethylsilyl cefamandole is a metastable pentahydrate which is readily converted to the more stable trihydrate.

The cefamandole hydrate can be readily converted to sodium cefamandole of excellent purity by reaction with sodium 2-ethylhexanoate or sodium acetate.

DETAIL DESCRIPTION AND PREFERRED EMBODIMENTS

According to the process of this invention crude cefamandole can be silylated to provide bis-trimethylsilyl cefamandole (Formula I), hereinafter named BTMS-cefamandole, by reaction with silylating agents selected from the following group:

N-trimethylsilylacetamide (MSA),
N,O-bis(trimethylsilyl)acetamide (BSA),
N,O-bis(trimethylsilyl)trifluoroacetamide (BSTA),
N-trimethylsilyl-N-methyltrifluoroacetamide or
N-trimethylsilyl imidazole (TMSI).

The use of silylating agents which produce bases as by-products such as hexamethyldisilazane should be avoided because they cause undesirable isomerization of the cephalosporin Δ³ double bond. The silylated acetamide reagents produce neutral acetamide by-products and therefore they are preferred. Especially preferred for silylating cefamandole in the process of this invention are MSA and BSA. Two trimethylsilyl equivalents are required to silylate both the hydroxyl and carboxyl functions of cefamandole. Therefore, two molar equivalents of MSA and one molar equivalent of BSA are sufficient for complete silylation of cefamandole when the reagents are in a pure state. However, it has been found that an excess of silylating agent is preferred to provide crystalline BTMS-cefamandole in good yields when the reagents are of commercial grade quality. Therefore, it is desirable to react cefamandole with a two fold excess or at least 4 molar equivalents of commerical grade MSA. Usually one molar equivalent or a slight excess of commercial grade BSA is satisfactory for efficient silylation, the BSA being of better quality than MSA apparently.

The silylation can be carried out at ambient temperature in a substantially anhydrous inert solvent such as ethyl acetate. By substantially anhydrous is meant that only trace amounts of water are permitted which will not materially affect the primary reaction. Ethyl acetate is preferred as a solvent because BTMS-cefamandole is only slightly soluble in said solvent, precipitates as a crystalline product from the reaction mixture, and is easily recovered by filtration. Unreacted materials and silylated impurities remain in the solvent solution. Because of the unique hydrophobic character of BMTS-cefamandole which renders it stable to water the acetamide by-product which often coprecipitates with the product is conveniently separated by washing with water. The silylation reaction is exothermic and when carried out at ambient temperature the temperature of the reaction mixture rises to about 40° C. Although the reaction can be carried out at temperatures between 0° and 80° C. ambient temperature is preferred. The formation of BTMS-cefamandole product is rapid at ambient temperature and usually the product begins to precipitate within minutes of the addition of the reagents. Preferably the reaction is completed within two hours but longer reaction times can be used, although no improvement in yields accrues thereby. The quality of the BTMS-cefamandole obtained by the process described above is of sufficient purity for conversion to crystalline cefamandole. However BTMS-cefamandole can be recrystallized from ethyl acetate neat or from chloroform or methylene chloride by precipitation with n-hexane if it is desired or necessary to separate other organic impurities.

BTMS-Cefamandole can be prepared ab initio from tetrazole nucleus by first silylating the nucleus and then acylating with D-anhydro O-carboxymandelic acid in substantially anhydrous ethyl acetate. Two trimethylsilyl equivalents are required for complete silylation of the nucleus to provide trimethylsilyl 7-trimethylsilylamino-3-(1-methyl-1,2,3,4-tetrazol-5-yl)thiomethyl-3-cephem-4-carboxylate in situ. Two molar equivalents of MSA or one equivalent of BSA or a slight excess thereof are preferred for silylation of the nucleus. With commercial grade MSA four molar equivalents are preferred for silylation. The silylation reaction proceeds rapidly at ambient temperature and the tetrazole nucleus goes into solution. Upon solution of the primary reactants the silylated nucleus is acylated preferrably with one molar equivalent or slight excess thereof of D-anhydro O-carboxymandelic acid. The acylation can be carried out by adding the silylated nucleus to the acylating agent or adding the acylating agent to the silylated nucleus. As the acylation proceeds the BTMS-cefamandole product precipitates out of solution and can be recovered by filtration. A unique result of the process is that the silylated product is obtained as a crystalline material which is stable to moisture and can be stored for propitious conversion to cefamandole pentahydrate or trihydrate as the case may be. The reaction conditions for the preparation of BTMS-cefamandole ab initio are analogous to those for the preparation from cefamandole as described hereinabove. The reactant ratios can be desirably varied according to the purpose, purity and cost of the reagents. For example excess silylating agent can be used to react with trace amounts of water in the reaction solvent. Recognizing that the cephalosporin reactant is the most expensive component, it is preferrable to use suitable excesses of the silylating or acylating reagents for more efficient conversion.

The BTMS-cefamandole obtained by either of the methods described above can be converted to cefamandole by hydrolysis. Alternatively BTMS-cefamandole can be converted by solvolysis to an isopropyl solvate which in turn can be hydrolyzed to cefamandole under very mild conditions. In either case cefamandole pentahydrate is recovered as the primary product of the hydrolysis. However, cefamandole pentahydrate is a metastable material which can be easily converted to the more stable trihydrate form upon heating or prolonged drying. Therefore, it is more convenient to simply convert the hydrolysis product to cefamandole trihydrate by drying.

Since BTMS-cefamandole is virtually insoluble in water, aqueous solvent mixtures are preferred for the hydrolysis. The silyl compound can be reacted with water admixed with ethanol or isopropanol. The hydrolysis can be best accomplished by heating the silyl compound in said solvent mixtures at the boiling temperature. Once solution of the silyl compound is achieved by heating, hydrolysis occurs at a rapid rate and is completed in a short time, usually within minutes. The pentahydrate compound can be recovered by evaporation of the solvents in vacuo or crystallization from solution by cooling. Upon drying the pentahydrate is converted to the more stable cefamandole trihydrate.

BTMS-Cefamandole can also be reacted with isopropanol admixed with a primary alcohol selected from methanol, ethanol, propanol or butanol to form an isopropyl solvate. Cefamandole isopropyl solvate is readily hydrolyzed to cefamandole by reaction with cold water. Again the hydrolysis product can be recovered as cefamandole pentahydrate which upon drying is converted to the trihydrate.

The following examples further illustrate the intermediates, compounds and processes of this invention.

EXAMPLE 1

Bis-Trimethylsilyl Cefamandole via Cefamandole 7-(D-Mandelamido)-3-(1-methyl-1,2,3,4-tetrazol-5-yl)thiomethyl-3-cephem-4-carboxylic acid, 4.0 g (8.6 mmoles), 5.4 g (34.4 mmoles) of N-trimethylsilylacetamide, and 50 ml of ethyl acetate were stirred for 2 hours at room temperature. The precipitated product was filtered and dried in vacuo. The crude product was washed with water, dried and recrystallized from a mixture of chloroform and n-hexane to yield 3.3 g (63.5 percent) of trimethylsilyl 7-[D-O-(trimethylsilyl)mandelamido]-3-(1-methyl-1,2,3,4-tetrazol-5-yl)thiomethyl-3-cephem-4-carboxylate.

Analysis $C_{24}H_{34}N_6O_5S_2Si_2$ MW 606.

Calcd: C, 47.55; H, 5.65; N, 13.87; S, 10.58. Found: C, 47.73; H, 5.40; N, 14.02; S, 10.86.

EXAMPLE 2

Bis-Trimethylsilyl Cefamandole via Tetrazole Nucleus

In this example the acylating agent is added to the silylated tetrazole nucleus.

Eight grams (24.4 mmoles) of 7-amino-3-(1-methyl-1,2,3,4-tetrazol-5-yl)thiomethyl-3-cephem-4-carboxylic acid, 12.8 g (97.6 mmoles) of N-trimethylsilylacetamide, and 100 ml of ethyl acetate were stirred at room temperature until the reactants dissolved. D-anhydro O-carboxymandelic acid, 4.77 g (26.8 mmoles), as a solution in ethyl acetate was added to the stirred reaction mixture. The reaction was stirred for 2 hours and seeded with trimethylsilyl cefamandole (Example 1). The product precipitated from solution and was filtered. The crude product was washed with water to remove acetamide and dried. The product was recrystallized from a mixture of methylene chloride and n-hexane to yield trimethylsilyl 7-[D-(O-trimethylsilyl)mandelamido]3-(1-methyl-1,2,3,4-tetrazol-5-yl)thiomethyl-3-cephem-4-carboxylate.

Analysis $C_{24}H_{34}N_6O_5S_2Si_2$ MW 606

Calcd: C, 47.55; H, 5.65; N, 13.87; N, 10.43. Found: C, 46.12; H, 5.22; N, 13.89; N, 10.58.

EXAMPLE 3

Cefamandole Isopropyl Solvate

Trimethylsilyl 7-[D-(O-trimethylsilyl)mandelamido]-3-(1-methyl-1,2,3,4-tetrazol-5-yl)thiomethyl-3-cephem-4-carboxylate, 23.2 g, was dissolved in 75 ml of ethanol by boiling. The homogeneous solution was diluted with 500 ml of isopropanol and allowed to cool. The solution was concentrated in vacuo. The residue was dissolved in 250 ml of isopropanol, filtered and cooled to yield 14.85 g of 7-(D-mandelamido)-3-(1-methyl-1,2,3,4-tetrazol-5-yl)thiomethyl-3-cephem-4-carboxylic acid isopropyl solvate after filtration. A sample of the product gave an NMR spectrum consistent with the isopropyl solvate of cefamandole.

EXAMPLE 4

Cefamandole Pentahydrate

One gram of trimethylsilyl 7-[D-(O-trimethylsilyl)mandelamido]-3-(1-methyl-1,2,3,4-tetrazol-5-yl)thiomethyl-3-cephem-4-carboxylate was dissolved in aqueous ethanol (2 ml of water, 25 ml ethanol) by boiling and heating for 10 minutes. The solution was diluted with 50 ml of water and cooled. The product crystallized to yield 0.9 g of 7-(D-mandelamido)-3-(1-methyl-1,2,3,4-tetrazol-5-yl)thiomethyl-3-cephem-4-carboxylic acid pentahydrate. A sample of the product gave an NMR spectrum (deuteroacetone) consistent with cefamandole pentahydrate and indicating the absence of the trimethylsilyl groups.

EXAMPLE 5

Bis-Trimethylsilyl Cefamandole via BSA

Four hundred and fifty four grams (0.98 mole) of cefamandole acid was added to a solution of 219.79 (1.08 moles) of N,O-bis(trimethylsilyl)acetamide (BSA) in 2300 ml of ethyl acetate. Within a few minutes the silyl derivative began to crystallize from solution. The mixture was stirred for about 2 hours. The insoluble product was filtered to yield 412.2 g (69.4 percent) of trimethylsilyl 7-[D-(O-trimethylsilyl)mandelamido]-3-(1-methyl-1,2,3,4-tetrazol-5-yl)thiomethyl-3-cephem-4-carboxylate.

EXAMPLE 6

Bis-Trimethylsilyl Cefamandole via Silylated Tetrazole Nucleus

In this example the tetrazole nucleus is first silylated and then added to the acylating agent. Eight grams (24.4 mmoles) of tetrazole nucleus, 7-amino-3-(1-methyl-1,2,3,4-tetrazol-5-yl)thiomethyl-3-cephem-4-carboxylic acid, were reacted with 12.8 g (97.6 mmoles) of N-trimethylsilylacetamide in 45 ml of ethyl acetate at 60° C until solution occurred. The mixture was allowed to cool to room temperature. The solution of silylated nucleus was added to 2.82 g (15.8 mmoles) of D-anhydro O-carboxymandelic acid in 35 ml of ethyl acetate at ambient temperature and stirred for 2 hours. The insoluble product was filtered and dried in vacuo. The silyl product was washed in 300 ml of water to remove acetamide. The material was dried to yield 7.4 g of trimethylsilyl 7-[D-(O-trimethylsilyl)mandelamido]3-(1-methyl-1,2,3,4-tetrazol-5-yl)thiomethyl-3-cephem-4-carboxylate.

EXAMPLE 7

Conversion of Cefamandole Isopropyl Solvate to Cefamandole Trihydrate

Cefamandole isopropyl solvate (Ex. 3), 3.85 g, was stirred for 1 hour with a mixture of water (300 ml) and ice. The insoluble product was filtered and dried in vacuo to yield 3.1 g of material. A sample of the product was subjected to X-ray powder analysis. The X-ray pattern was identical to that of an authentic sample of cefamandole trihydrate.

EXAMPLE 8

Bis-Trimethyl Cefamandole via N-(Trimethylsilyl)imidazole

Ten millimoles (4.62 g) of 7-(D-mandelamido)-3-(1-methyl-1,2,3,4-tetrazol-5-yl)thiomethyl-3-cephem-4-carboxylic acid were added to a solution of ethyl acetate (25 ml) and 4 ml (3.0 mmoles) of N-(trimethylsilyl imidazole. Upon solution of the reactants the product began to precipitate. The mixture was stirred for an hour. The insoluble product was filtered and washed with ethyl acetate and ether. The product was dried in vacuo to yield 6.06 g (45 percent) of trimethylsilyl 7-[D-O-(trimethylsilyl)mandelamido]-3-(1-methyl-1,2,3,4-tetrazol-5-yl)thiomethyl-3-cephem-4-carboxylate. A sample of the product gave an NMR spectrum identical to the spectrum of BTMS-cefamandole which was obtained by the method of Example 1.

EXAMPLE 9

Bis-Trimethyl Cefamandole via N,O-bis(Trimethylsilyl)trifluoroacetamide

Two and one half grams (5.4 mmoles) of 7-(D-mandelamido)-3-(1-methyl-1,2,3,4-tetrazol-5-yl)thiomethyl-3-cephem-4-carboxylic acid were added to a mixture of ethyl acetate (15 ml) and 3.5 ml of N,O-bis(trimethylsilyl)trifluoroacetamide. The mixture was stirred for 2 hours. The precipitated product was filtered and dried in vacuo to yield 2.0 g (61 percent) of trimethylsilyl 7-[D-O-(trimethylsilyl) mandelamido]-3-(1-methyl-1,2,3,4-tetrazol-5-yl thiomethyl-3-cephem-4-carboxylic acid. A sample of the product gave an NMR spectrum identical to the spectrum of BTMS-cefamandole which was obtained by the method of Example 1.

I claim:

1. A compound of the formula

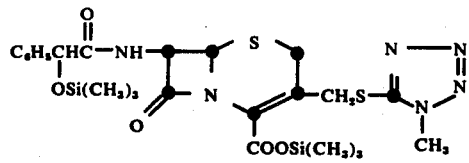

which is trimethylsilyl 7-[D-(O-trimethylsilyl)mandelamido]-3-(1-methyl-1,2,3,4-tetrazol-5-yl)thiomethyl-3-cephem-4-carboxylate.

2. The process for preparing the compound of claim 1 which comprises reacting 7-amino-3-(1-methyl-1,2,3,4-tetrazol-5-yl)-3-cephem-4-carboxylic acid with a silylating agent selected from N-trimethylsilylacetamide N,O-bis(trimethylsilyl)acetamide, N,O-bis(trimethylsilyl)trifluoroacetamide, N-trimethylsilyl-N-methyltrifluoroacetamide or N-trimethylsilylimidazole and acylating the product so formed with D-anhydro O-carboxymandelic acid in substantially anhydrous ethyl acetate.

3. The process for purifying cefamandole which comprises the steps of

A. reacting 7-(D-mandelamido)-3-(1-methyl-1,2,3,4-tetrazol-5-yl)-3-cephem-4-carboxylic acid with a silylating agent selected from N-trimethylsilylacetamide, N,O-bis(trimethylsilyl)acetamide, N,O-bis(trimethylsilyl)trifluoroacetamide, N-trimethylsilyl-N-methyltrifluoroacetamide or N-trimethylsilylimidazole in substantially anhydrous ethyl acetate to provide trimethylsilyl 7-[D-(O-trimethylsilyl)mandelamido]-3-(1-methyl-1,2,3,4-tetrazol-5-yl)thiomethyl-3-cephem-4-carboxylate; and B. reacting said silylated compound with (a) water admixed with ethanol or isopropanol or (b) isopropanol admixed with a primary alcohol selected from methanol, ethanol, propanol or butanol to provide 7-(D-mandelamido)-3-(1-methyl-1,2,3,4-tetrazol-5-yl)thiomethyl-3-cephem-4-carboxylic acid isopropyl solvate and reacting said isopropyl solvate with water; and recovering said cefamandole as a hydrate.

* * * * *